(12) United States Patent
Lee (10) Patent No.: US 8,824,243 B2
(45) Date of Patent: Sep. 2, 2014

(54) ULTRASONIC TRANSDUCER UNIT AND ULTRASONIC PROBE

(75) Inventor: Seung-Mok Lee, Osaka (JP)

(73) Assignee: Ingen MSL Inc., Izumi-Shi (JP)

( * ) Notice: Subject to any disclaimer, the term of this patent is extended or adjusted under 35 U.S.C. 154(b) by 8 days.

(21) Appl. No.: 13/581,465

(22) PCT Filed: Feb. 28, 2011

(86) PCT No.: PCT/JP2011/054498
§ 371 (c)(1),
(2), (4) Date: Oct. 2, 2012

(87) PCT Pub. No.: WO2011/105602
PCT Pub. Date: Sep. 1, 2011

(65) Prior Publication Data
US 2013/0016587 A1    Jan. 17, 2013

(30) Foreign Application Priority Data
Feb. 26, 2010   (JP) .................................. 2010-043454

(51) Int. Cl.
*B06B 1/02*    (2006.01)
*H02N 2/18*    (2006.01)

(52) U.S. Cl.
USPC .......................................... 367/140; 310/336

(58) Field of Classification Search
USPC .................................. 367/140, 181; 310/336
See application file for complete search history.

(56) References Cited

U.S. PATENT DOCUMENTS

| | | | |
|---|---|---|---|
| 8,398,551 B2 * | 3/2013 | Adachi et al. | 600/443 |
| 2007/0164632 A1 * | 7/2007 | Adachi et al. | 367/140 |
| 2008/0073998 A1 | 3/2008 | Sugiura et al. | |
| 2008/0139946 A1 * | 6/2008 | Adachi et al. | 600/463 |
| 2010/0242612 A1 | 9/2010 | Sano et al. | |
| 2011/0071396 A1 | 3/2011 | Sano et al. | |
| 2013/0016587 A1 * | 1/2013 | Lee | 367/140 |

FOREIGN PATENT DOCUMENTS

| | | | | |
|---|---|---|---|---|
| EP | 1761104 A1 * | 3/2007 | | B06B 1/02 |
| JP | 2008-085462 A | 4/2008 | | |
| WO | 2005/120130 A1 | 12/2005 | | |
| WO | WO 2005/120130 | * 12/2005 | | |
| WO | 2009/069555 A1 | 6/2009 | | |
| WO | 2009/139400 A1 | 11/2009 | | |
| WO | WO 2011/105602 | * 9/2011 | | |

OTHER PUBLICATIONS

Arif S. Ergun, Goksen G. Yaralioglu, and Butrus T. Khuri-Yakub, "Capacitive Micromachined Ultrasonic Transducers: Theory and Technology", Journal of Aerospace Engineering (c) ASCE, Apr. 2003, p. 76-84.

* cited by examiner

*Primary Examiner* — Daniel Pihulic
(74) *Attorney, Agent, or Firm* — Masuvalley & Partners (57) ABSTRACT

In an ultrasonic transducer unit comprising a plurality of ultrasonic transducers, each of the ultrasonic transducers is provided with a recess formed in one face of an insulating substrate, and a substrate-side electrode is buried in a bottom of the recess, and a vibrating membrane is formed so as to cover the recess.

8 Claims, 10 Drawing Sheets

ULTRASONIC TRANSDUCER UNIT AND ULTRASONIC PROBE

This application is a National Stage application under 35 U.S.C. §371 of International Application Serial No. PCT/JP2011/054498, filed on Feb. 28, 2011, and claims the priority benefit under 35 U.S.C. §119 of Japanese Patent Application No. 2010-043454, filed on Feb. 26, 2010, which are hereby expressly incorporated by reference in their entirety for all purposes.

FIELD OF THE INVENTION

The present invention relates to an ultrasonic transducer unit and an ultrasonic probe using the ultrasonic transducer.

BACKGROUND OF THE INVENTION

Figure 1:
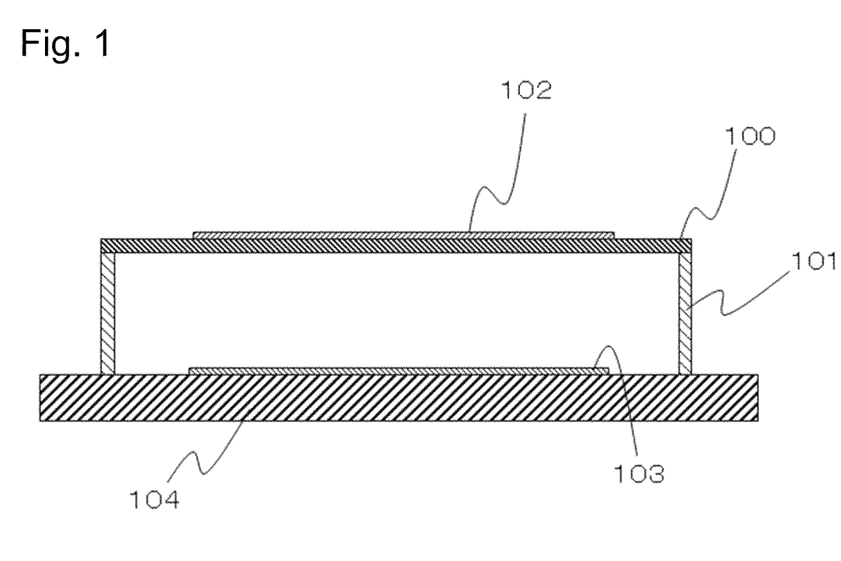
FIG. 1 is a sectional view showing an example of a configuration of the conventional CMUT-type ultrasonic transducer.

FIG. 1 is a sectional view showing an example of a configuration of the conventional CMUT (Capacitive Micromachined Ultrasonic Transducer)-type ultrasonic transducer. The conventional CMUT-type ultrasonic transducer comprises a vibrating membrane 100 which sends and receives an ultrasonic wave, and a vibrating membrane supporting section 101 which is provided on one face of a substrate 104 and supports the vibrating membrane 100 so that the vibrating membrane 100 faces the substrate 104. A membrane-side electrode 102 is formed on the vibrating membrane 100, a substrate-side electrode 103 is formed on the substrate 104, and the membrane-side electrode 102 and the substrate-side electrode 103 are arranged opposite to each other.

In such a CMUT-type ultrasonic transducer, the vibrating membrane 100 and the membrane-side electrode 102 vibrate by the received ultrasonic wave (sound pressure). In this case, the CMUT-type ultrasonic transducer obtains an electric signal for the received ultrasonic wave based on a capacitance change between the membrane-side electrode 102 and the substrate-side electrode 103, or applies DC voltage and AC voltage between the membrane-side electrode 102 and the substrate-side electrode 103, thereby causing the vibrating membrane 100 to vibrate and transmitting an ultrasonic wave. The CMUT-type ultrasonic transducer has a frequency response characteristic such as a wideband, a high sensitivity, and the like.

For example, the conventional CMUT-type ultrasonic transducer and a method for manufacturing the same are disclosed in "Capacitive Micromachined Ultrasonic Transducers: Theory and Technology", JOURNAL OF AEROSPACE ENGINEERING, USA, April, VOL. 16, NO. 2, p. 76-84. In detail, in the CMUT-type ultrasonic transducer, a nitride layer for protecting the substrate is formed on a silicon substrate in a case of later-described wet etching, and the so-called sacrificial layer containing polycrystalline silicon is vapor-deposited on the nitride layer. Then, both a vibrating membrane containing a nitride layer and a vibrating membrane supporting section are vapor-deposited on the above-mentioned sacrificial layer, and a hole for removing the sacrificial layer is formed on the vibrating membrane. Via the hole, an etching solution is poured in and the sacrificial layer is removed by wet etching. Subsequently, the hole is filled, a membrane-side electrode is vapor-deposited on the vibrating membrane, and then a protective layer is formed on the membrane-side electrode to produce the CMUT-type ultrasonic transducer.

SUMMARY OF THE INVENTION

Problem(s) to be Solved by the Invention

However, in the ultrasonic transducer disclosed in "Capacitive Micromachined Ultrasonic Transducers Theory and Technology", JOURNAL OF AEROSPACE ENGINEERING, USA, April, VOL. 16, NO. 2, p. 76-84, there is a problem of needing a plurality of processes, such as a process of forming the so-called sacrificial layer, a process of forming the hole in the vibrating membrane for etching, a process of removing the sacrificial layer by wet etching or vapor etching, and a process of filling the hole, in order to provide a space between the membrane-side electrode and the substrate-side electrode.

Moreover, the wet etching is a time-consuming process, and a protection layer is need in a case that the etching selectivity between the patterned resist layer and the etching material is not so large. Therefore, a manufacturing process becomes complicated, and such a problem is also occurred in the vapor etching.

From these facts, the wet etching or vapor etching process reduces the reproducibility and reliability of the CMUT which are essential in the mass production.

Furthermore, since the ultrasonic transducer disclosed in "Capacitive Micromachined Ultrasonic Transducers: Theory and Technology", JOURNAL OF AEROSPACE ENGINEERING, USA, April, VOL. 16, NO. 2, p. 76-84 has the membrane supporting structure for the vibration of membrane, which also play a role of fixing the vibrating membrane to the substrate (for example, control of stress generation at a fixed portion).

The present invention has been made with the aim of solving the above problems, and it is an object of the invention to provide an ultrasonic transducer unit comprising a plurality of ultrasonic transducers on an insulating substrate, each of the ultrasonic transducers which is provided with a substrate-side electrode provided on one face side of the substrate, with a vibrating membrane arranged so that one face of the vibrating membrane faces the substrate-side electrode, and with a film-side electrode provided on the other face of the vibrating membrane, thereby allowing for the manufacturing at high reproducibility, reliability, and the simplified manufacturing processes, and to provide an ultrasonic probe comprising the ultrasonic transducer unit.

Means for Solving the Problem

The ultrasonic transducer unit according to the present invention is an ultrasonic transducer unit comprising a plurality of ultrasonic transducers on an insulating substrate, each of the ultrasonic transducers which is provided with a substrate-side electrode provided on one face side of the substrate and with a vibrating membrane having an electric conductivity and arranged so that one face of the vibrating membrane faces the substrate-side electrode, wherein said ultrasonic transducer is provided with a recess formed in one face of the substrate, said substrate-side electrode is provided in a bottom of the recess, and said vibrating membrane is provided so as to cover the recess.

In the present invention, an ultrasonic wave is transmitted and received based on the variation of electrostatic capacitance between the vibrating membrane having an electric conductivity and the substrate-side electrode buried in the bottom of the recess of the ultrasonic transducer due to the change of a space between the vibrating membrane and the substrate-side electrode. Note that the substrate-side electrode is buried in the bottom of the recess, and thereby a thinner unit of the substrate is achieved.

The ultrasonic transducer unit according to the present invention is characterized in that said vibrating membrane is fixed to a land part provided by the recesses of the ultrasonic transducers by electrostatic attraction and chemical bonding.

In the present invention, the vibrating membrane is fixed to the land part by the anodic bonding method, for example. Therefore, the vibrating membrane is fixed to the land part by the electrostatic attraction and the chemical bonding, thereby the bonding force is so high, and the stress generation on the vibrating membrane and the land part is suppressed.

The ultrasonic transducer unit according to the present invention is characterized in that said substrate-side electrode is buried in the bottom of the recess, a groove which connects the recesses of the ultrasonic transducers is formed in the land part, and a connection electrode which connects the substrate-side electrodes of the ultrasonic transducers is buried in a bottom of the groove and the bottom of the recess.

In the present invention, the substrate-side electrode is buried in the bottom of the recess, a groove which connects the recesses of the ultrasonic transducers to each other is formed, and the connection electrode is also buried in the bottoms of the groove and the recess, thereby the connection of the substrate-side electrodes in a simple structure is achieved, and also a thinner unit of the substrate is achieved.

The ultrasonic transducer unit according to the present invention is characterized in that said substrate-side electrode protrudes in the bottom of the recess, a groove which connects the recesses of the ultrasonic transducers is formed in the land part, and a connection electrode which connects the substrate-side electrodes of the ultrasonic transducers to each other protrudes in a bottom of the groove and the bottom of the recess.

In the present invention, the substrate-side electrode protrudes in the bottom of the recess, a groove which connects the recesses of the ultrasonic transducers to each other is formed, and the connection electrode protrudes in the bottoms of the groove and the recess, thereby the connection of the substrate-side electrodes in a simple structure is achieved, and also a thinner unit of the substrate is achieved.

The ultrasonic transducer unit according to the present invention is characterized in that a through hole is formed in the vibrating membrane at a position conforming the groove, a protection film formed on the other side of the vibrating membrane, and an isolation film including an object which is vapor-deposited via the through hole, and isolating the adjacent ultrasonic transducers from each other is formed inside the groove.

In the present invention, since the groove is formed in the land part, the adjacent ultrasonic transducers communicate with each other via the groove. However, since a vapor-deposition object is vapor-deposited inside the groove via the through hole to form the isolation film, the adjacent ultrasonic transducers are isolated from each other, and the acoustical influence from the adjacent ultrasonic transducers could be prevented beforehand.

The ultrasonic transducer unit according to the present invention is characterized in that said vibrating membrane is fixed to the land part by an anodic bonding method.

In the present invention, the vibrating membrane is fixed to the land part using the anodic bonding method at a temperate of 400 degrees or less, for example. Therefore, the vibrating membrane is fixed to the land part by the electrostatic attraction and the chemical bonding. Compared with the bonding at a high temperature of 800-1000 degrees or the bonding using pressure only, a high bonding force could be obtained even at a low temperature, the occurrence of the stress in a bonded portion is controlled, and the stress in the whole vibrating membrane and the substrate decreases.

Moreover, it is preferred that the vibrating membrane includes silicon single crystal.

The ultrasonic probe according to the present invention is an ultrasonic probe comprising an ultrasonic transducer unit according to the present invention, wherein the ultrasonic probe sends and receives an ultrasonic wave using said ultrasonic transducer unit.

In the present invention, voltage is applied between the substrate-side electrode and the vibrating membrane of each of the plurality of ultrasonic transducers provided in the ultrasonic transducer unit of the present invention. Thereby, the vibrating membrane vibrates to transmit an ultrasonic wave to the outside, and an electric signal concerning the capacitance change between the substrate-side electrode and the vibrating membrane due to the vibration of the substrate (or the vibrating membrane) by the ultrasonic wave reflected from the outside can be obtained, i.e., data concerning the ultrasonic image can be obtained.

Effect of the Invention

According to the present invention, the process of forming a sacrificial layer, the process of forming a hole, the time-consuming process of etching the sacrificial layer, etc. can be omitted. Moreover, there is no possibility of damage to the vibrating membrane due to the vapor etching, and the manufacturing at high reproducibility, reliability, and the simplified process can be achieved. Furthermore, it is not necessary to form separately the vibrating membrane supporting section which supports the vibrating membrane so as to vibrate, therefore it is not necessary to consider the stress concentration in a fixed portion occurring when the vibrating membrane supporting section is fixed to the substrate, etc., and the flexibility in manufacture increases.

According to the present invention, since the vibrating membrane is fixed to the land part by the electrostatic attraction and the chemical bonding, the stress occurring in a portion in which the land part is fixed to the vibrating membrane can be controlled, and the stress occurring in the whole of the vibrating membrane and the substrate can be reduced. Therefore, the so-called conversion efficiency or sensitivity can be improved.

THE CONFIGURATION FOR INVENTING

The following description will explain an ultrasonic transducer unit and an ultrasonic probe according to the present invention, based on the drawings in detail.

Embodiment 1

Figure 2:
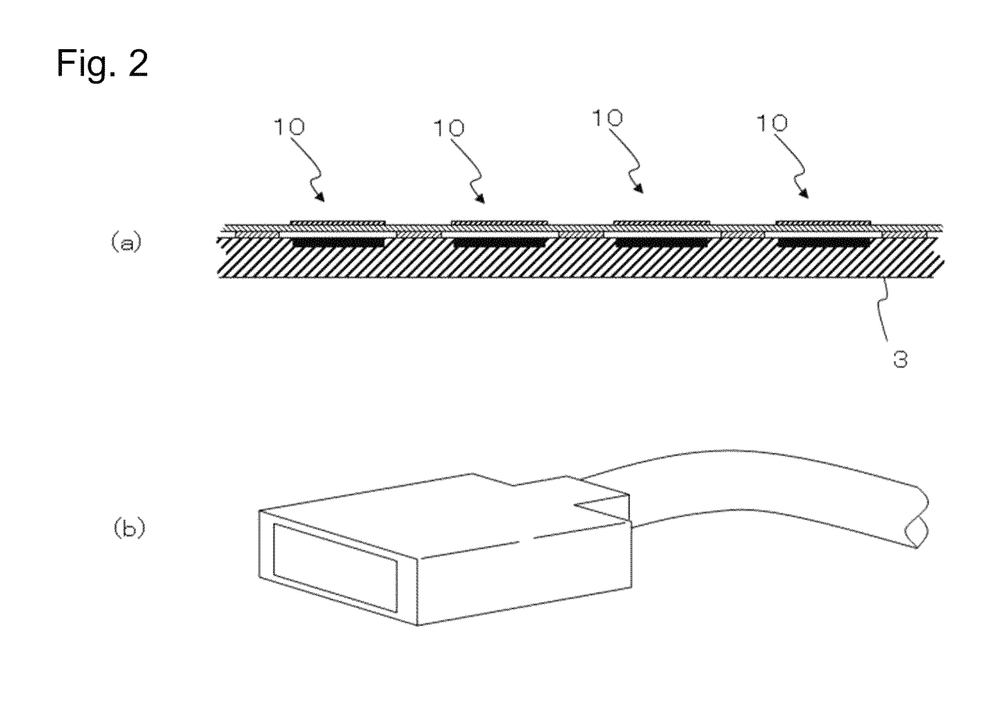
FIG. 2 is a schematic partial sectional view (*a*) showing an ultrasonic transducer unit according to Embodiment 1 of the present invention, and an illustrative view (*b*) showing an example of an ultrasonic probe comprising the ultrasonic transducer unit.

FIG. 2 is a schematic partial sectional view (*a*) showing the ultrasonic transducer unit according to Embodiment 1 of the present invention, and an illustrative view (*b*) showing an example of the ultrasonic probe comprising the ultrasonic transducer unit. In the ultrasonic transducer unit according to the present invention, a plurality of ultrasonic transducers 10 are provided on a substrate 3 in a pattern state (refer to FIG. 2 (*a*)). The ultrasonic probe according to the present invention (refer to FIG. 3 (*b*)) comprises the ultrasonic transducer unit, and transmits an electric signal concerning an ultrasonic wave received by the ultrasonic transducer unit to an external device, for example.

Figure 3:
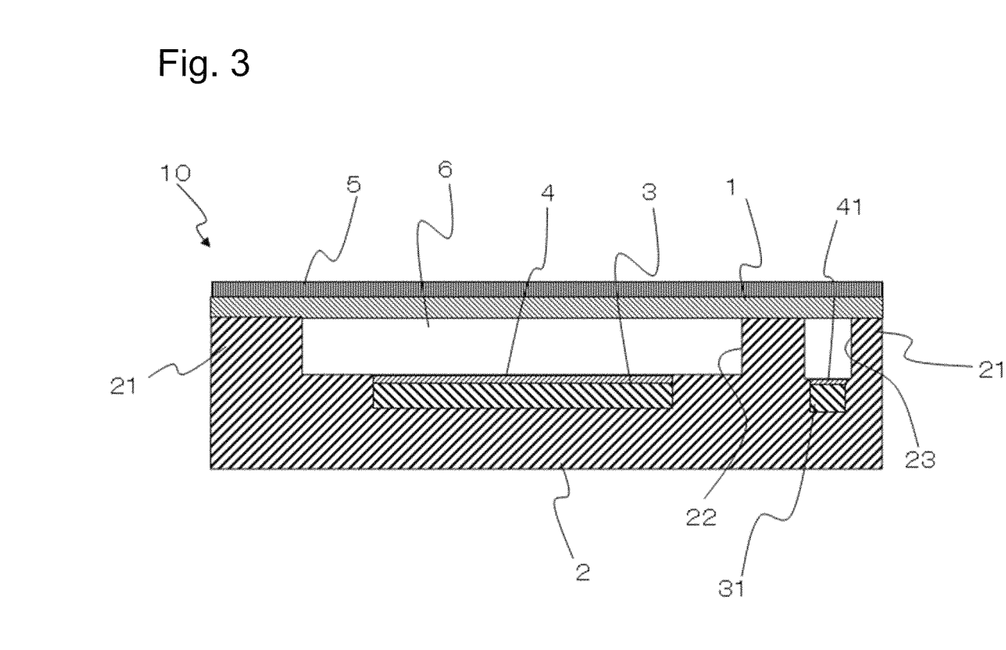
FIG. 3 is a schematic sectional view for explaining a configuration of an ultrasonic transducer provided in the ultrasonic transducer unit according to Embodiment 1 of the present invention.
Figure 4:
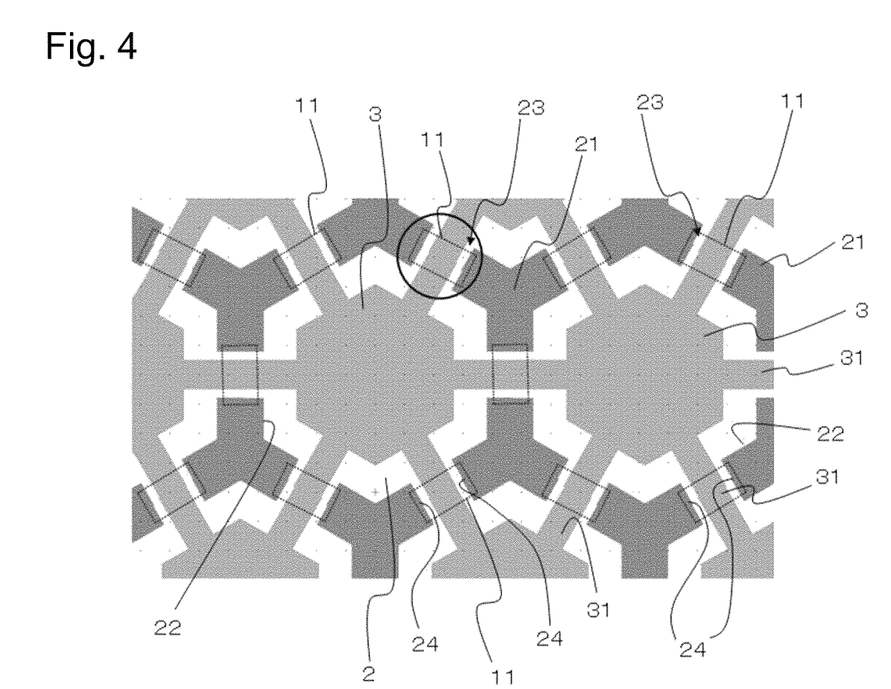
FIG. 4 is a top view showing a state in which a vibrating membrane of the ultrasonic transducer provided in the ultrasonic transducer unit according to Embodiment 1 of the present invention is removed.

FIG. 3 is a schematic sectional view for explaining a configuration of an ultrasonic transducer provided in the ultrasonic transducer unit according to Embodiment 1 of the present invention. FIG. 4 is a top view showing a state in which a vibrating membrane of the ultrasonic transducer provided in the ultrasonic transducer unit according to Embodiment 1 of the present invention is removed.

The ultrasonic transducer 10 of the ultrasonic transducer unit according to Embodiment 1 of the present invention comprises a substrate 2, and a vibrating membrane 1 which is arranged on an upper side of the substrate 2 to face the substrate 2 and transmits or receives an ultrasonic wave. A protective film 5 for protecting the vibrating membrane 1 is vapor-deposited on an upper face of the vibrating membrane 1, and a recess 22 is formed on an upper face of the substrate 2 facing a lower face of the vibrating membrane 1. A substrate-side electrode 3 is buried in a bottom of the recess 22, and the vibrating membrane 1 is arranged on an upper side of the recess 22. The vibrating membrane 1 and the recess 22 form a space part 6.

A plurality of the ultrasonic transducers 10 of such a configuration are provided on the upper face of the substrate 2, and function as an ultrasonic transducer unit according to Embodiment 1 of the present invention.

The substrate 2 is made of glass, such as the Pyrex glass (registered trademark), quartz, the tempax (registered trademark), and the Foturan glass (registered trademark), and has a thickness of 500 micrometers or more. As mentioned above, the recess 22 is formed on the upper face of the substrate 2, and the substrate-side electrode 3 is buried in the bottom of recess 22. A later-described groove 23 is also formed on the upper face of the substrate 2, and a later-described connection electrode 31 is buried in a bottom of the groove 23.

The thickness of the substrate 2 is not restricted to the above description. For example, it may be 300 micrometers or more and 500 micrometers or less.

The recess 22 is provided on the upper face of the substrate 2 so that it has a hexagonal form in a plane view. Between the recesses 22 of the ultrasonic transducers 10, a land part 21 consisting of a residual part of the substrate 2 which is remaining after forming the recesses 22 is formed. The vibrating membrane 1 is fixed to the upper faces of the land parts 21, i.e., the upper face of the substrate 2. The substrate-side electrode 3 is buried in a center of the bottom of the recess 22.

The substrate-side electrode 3 has a form of a hexagonal plate in the same manner as the recess 22, and an area of 700-micrometer$^2$ or less. The substrate-side electrode 3 has a thickness of 0.1-1.0 micrometer, and made of a material, such as Ni, Cr, Al, Pt, and Au, for example. An insulating film 4 which is made of an oxide, for example, and insulates the substrate-side electrode 3 from the vibrating membrane 1 is vapor-deposited on an upper face of the substrate-side electrode 3. The insulating film 4 is flush with the bottom of the recess 22 in this state.

The substrate-side electrodes 3 of the ultrasonic transducers 10 are connected to the substrate-side electrodes 3 of the adjacent ultrasonic transducers 10 via a plurality of the connection electrodes 31, 31, . . . , 31. Each of the connection electrodes 31 is a strip-shaped plate of the same material as the substrate-side electrode 3, and is buried in the bottom of the recess 22. In the same manner as the substrate-side electrode 3, an insulating film 41 which is made of an oxide, for example, and insulates the connection electrode 31 from the vibrating membrane 1 is vapor-deposited on an upper face of the connection electrode 31, and the connection electrodes 31, 31, . . . , 31 extend from the edges of the substrate-side electrodes 3 in a plane direction of the substrate-side electrodes 3. Note that the material of the connection electrode 31 is not restricted to the same material as the substrate-side electrode 3, and a vapor deposited material having electrical conductivity could be used.

One side of an inner side of the recess 22 is 22 micrometers, for example, and the inner side of the recess 22 has a form of a hexagonal tube whose distance between opposing sides is 38 micrometers. The form of the recess 22 is not restricted to the form of the hexagonal tube, and could be made as a circular tube.

The grooves 23 are formed at a plurality of sites of the land part 21 by cutting parts of the land part 21 in a lengthwise direction. In detail, the grooves 23 are formed at positions corresponding to the respective sides of the recess 22 having the hexagonal form, respectively, and the recesses 22 of the adjacent ultrasonic transducers 10 are connected to each other via the grooves 23. End parts 24 of the land parts 21 face each other with the grooves 23 there between. Moreover, the connection electrode 31 is buried in the bottom of each groove 23. That is, the connection electrode 31 is buried over the bottoms of the recess 22 and groove 23, and connects the substrate-side electrodes 3 to each other.

The land part 21 may have a size in the lengthwise direction of 0.05-10 micrometers (in other words, a distance between the lower face of the vibrating membrane 1 and the upper face of the substrate 2 may be 0.05-10 micrometers). It is preferred that the size in the lengthwise direction is 0.1-3 micrometers. The land part 21 has a thickness in a lateral direction thereof of 8-16 micrometers. Note that the lower face of the vibrating membrane 1 is bonded to the upper face of the land part 21 (that is, the upper face of the substrate 2), by a so-called anodic bonding method.

The anodic bonding is a bonding method between glass and silicon or metal generally at a temperature of about 400 degrees or lower. The method is performed by piling up glass and silicon or metal, and applying heat and voltage to them. Thereby, a cation in glass is forcedly diffused to silicon or metal, electrostatic attraction arises between glass and silicon or metal, and glass and silicon or metal are chemically bonded. Therefore, the method is a method capable of a satisfactory bonding even at a relatively low temperature.

Such the anodic bonding method is used for the ultrasonic transducer 10 of the ultrasonic transducer unit according to Embodiment 1 of the present invention, thereby controlling that the stress concentration by the deformation which tends to occur in the bonding process at a high temperature arises at a part where the land part 21 and the vibrating membrane 1 are bonded, and preventing the lowering of the conversion efficiency or sensitivity due to the stress, and also achieving the excellent structure reproducibility in manufacturing.

Although the case in which the land part 21 has the thickness of 8-16 micrometers is described as an example in Embodiment 1, the thickness is not restrict to this and may be 3-16 micrometers.

The vibrating membrane 1 is provided so as to cover the recess 22. Therefore, the space part 6 is formed by an inner periphery of the recess 22 and the lower face of the vibrating membrane 1.

Although it is preferred that the vibrating membrane 1 has the thickness of 1.5 micrometers, the thickness may be 0.5-3 micrometers. The vibrating membrane 1 is made of silicon single crystal having electric conductivity. Therefore, in the ultrasonic transducer unit and the ultrasonic probe according to Embodiment 1 of the present invention, an electric charge accumulates in the vibrating membrane when voltage is applied. Moreover, the occurrence of the charge phenomenon can be prevented when the vibrating membrane is operated by applying AC voltage from several to several tens MHz.

Figure 5:
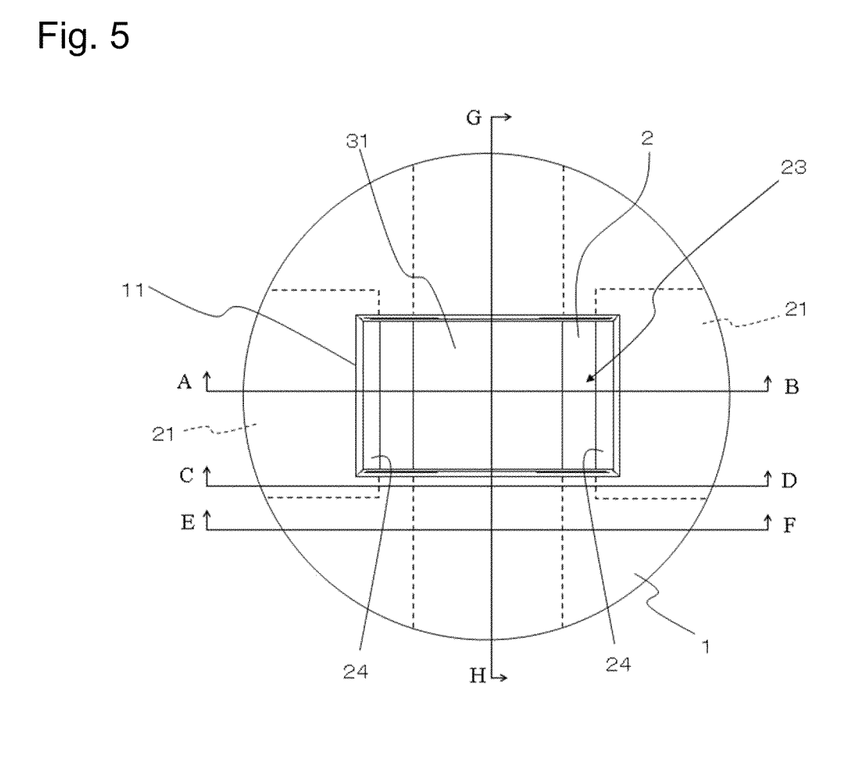
FIG. 5 is an enlarged view enlarging a portion corresponding to a position of a circle shown by a solid line in FIG. 4 in the ultrasonic transducer provided in the ultrasonic transducer unit according to Embodiment 1 of the present invention.
Figure 6:
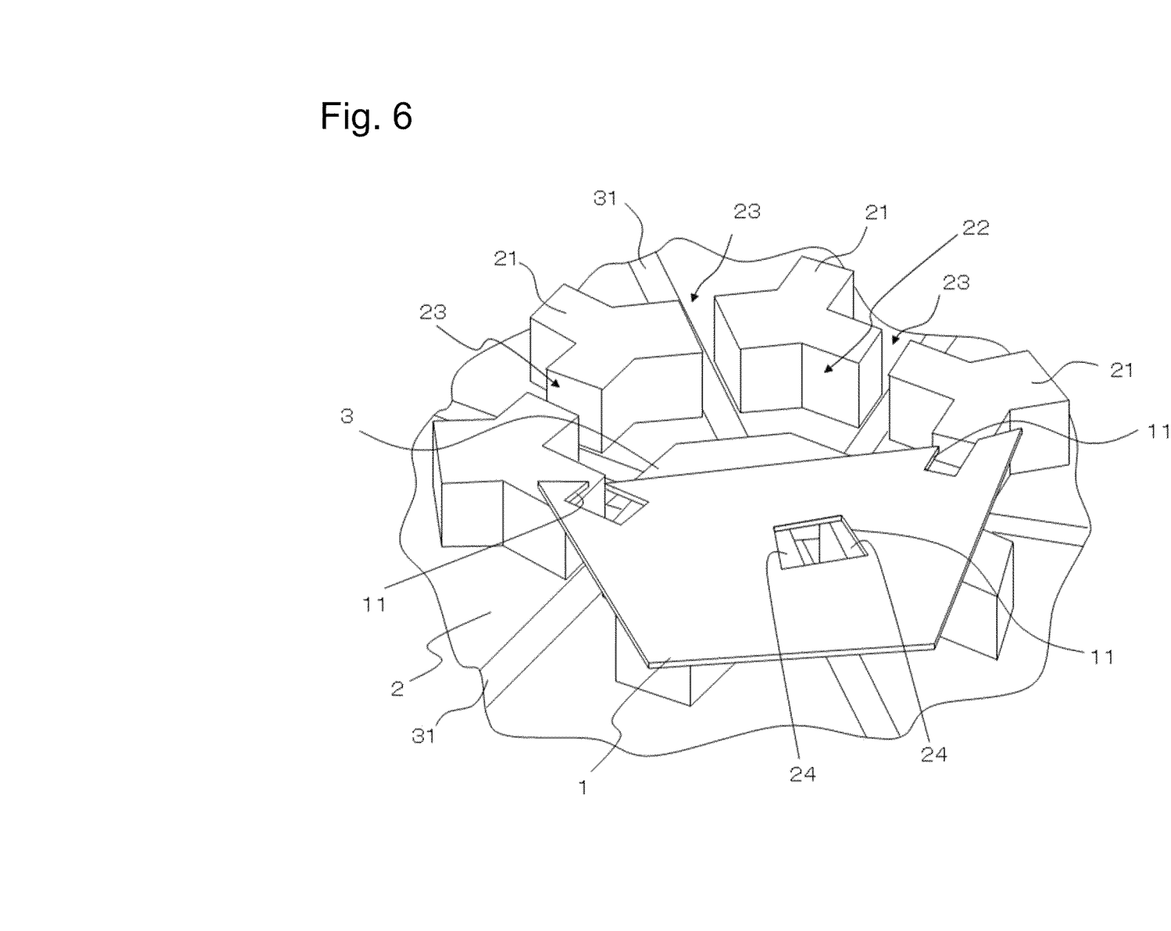
FIG. 6 is a partial perspective view showing a state in which a protective film and a vibrating membrane are partially removed in the ultrasonic transducer unit according to Embodiment 1 of the present invention.

A plurality of rectangular through holes 11 penetrating the vibrating membrane 1 in a thickness direction are formed in the vibrating membrane 1 at positions conforming the grooves 23, 23, ... , 23 of the land part 21 (in FIG. 4, the through holes 11 are shown by a dotted line). FIG. 5 is an enlarged view enlarging a portion corresponding to a position of a circle shown by a solid line in FIG. 4 in the ultrasonic transducer 10 provided in the ultrasonic transducer unit according to Embodiment 1 of the present invention. For convenience of explanation, FIG. 5 shows a state in which the protective film 5 is removed. FIG. 6 is a partial perspective view showing a state in which the protective film 5 and the vibrating membrane 1 are partially removed in the ultrasonic transducer unit according to Embodiment 1 of the present invention.

As mentioned above, the lower face of the vibrating membrane 1 contacts the upper face of the land part 21, and the vibrating membrane 1 is provided so as to cover the recess 22. The connection electrode 31 extends through the groove 23 provided between the land parts 21 and 21, and connects the substrate-side electrodes 3 to each other. Since the through hole 11 penetrates the vibrating membrane 1 in the thickness direction, a part of the groove 23, the end part 24 of the land part 21 and the connection electrode 31 are exposed via the through hole 11.

Figure 7:
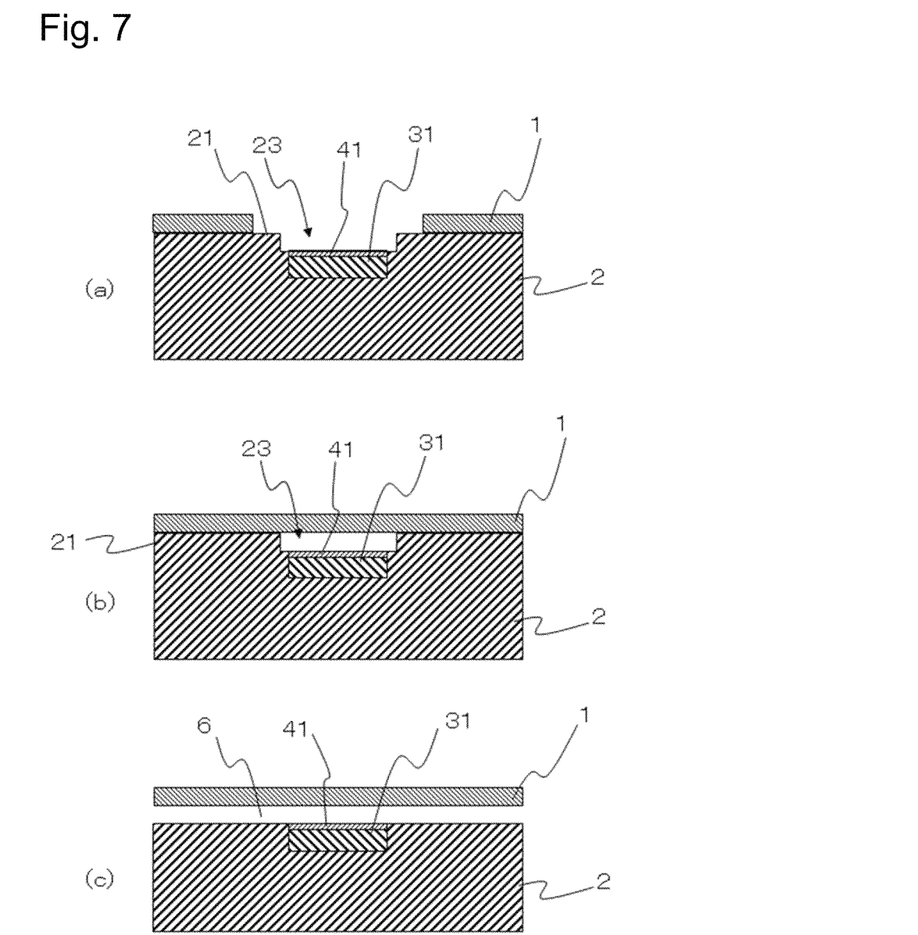
FIG. 7 is a longitudinal sectional view showing a part of the ultrasonic transducer provided in the ultrasonic transducer unit according to Embodiment 1 of the present invention, in which the protective film is not vapor-deposited.

FIG. 7 is a longitudinal sectional view showing a part of the ultrasonic transducer 10 provided in the ultrasonic transducer unit according to Embodiment 1 of the present invention, in which the protective film 5 is not vapor-deposited. In detail, FIG. 7 (a) is a longitudinal sectional view by the A-B line of FIG. 5, FIG. 7 (b) is a longitudinal sectional view by the C-D line of FIG. 5, and FIG. 7 (c) is a longitudinal sectional view by the E-F line of FIG. 5.

Figure 8:
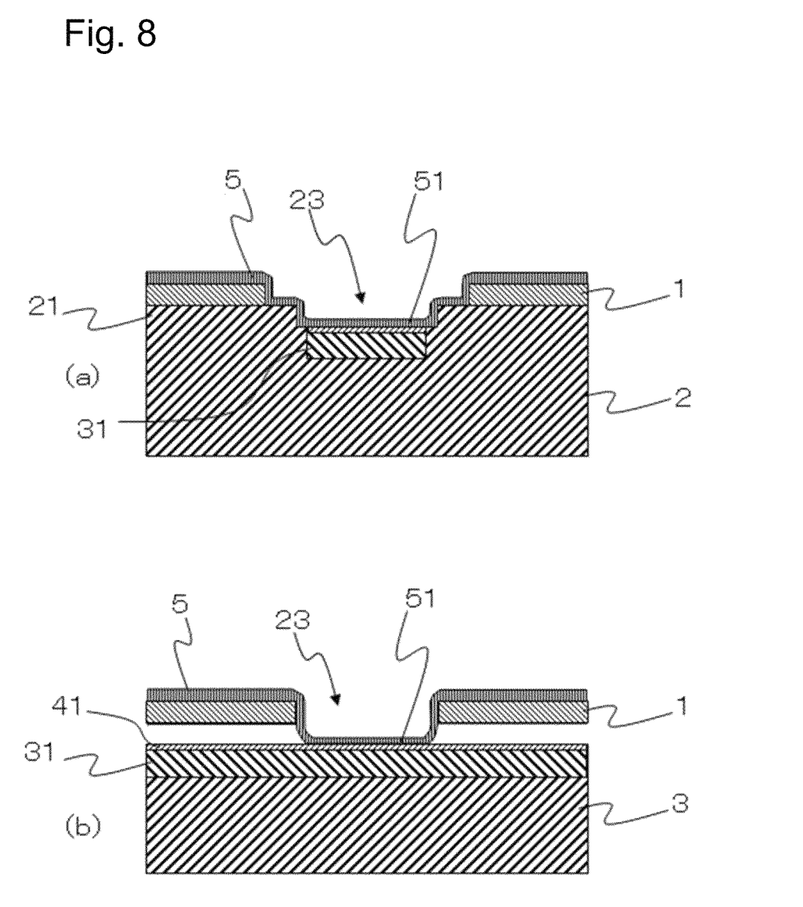
FIG. 8 is a longitudinal sectional view showing a part of the ultrasonic transducer provided in the ultrasonic transducer unit according to Embodiment 1 of the present invention, in which the protective film is vapor-deposited.

FIG. 8 is a longitudinal sectional view showing a part of the ultrasonic transducer 10 provided in the ultrasonic transducer unit according to Embodiment 1 of the present invention, in which the protective film 5 is vapor-deposited. In detail, FIG. 8 (a) is a longitudinal sectional view by the A-B line of FIG. 5, and FIG. 8 (b) is a longitudinal sectional view by the G-H line of FIG. 5.

The through hole 11 has a size in the longitudinal direction which is longer than a space between the end parts 24 and 24 of the land part 21 which counters across groove 23, and a size in the direction of the shorter side of the through hole 11 which is shorter than the thickness of land part 21. Therefore, as mentioned above, the end parts 24 and 24 of the land part 21 and a part of the connection electrode 31 are exposed via the through hole 11 and the groove 23 near the groove 23.

The protective film 5 and an isolation film 51 are formed by vapor-depositing an insulating vapor-deposition object, for example, in such a state. That is, the vapor-deposition object is vapor-deposited on the upper face of the vibrating membrane 1 to form the protective film 5, and is vapor-deposited on the inner side and the vicinity of the groove 23 via the through hole 11 to form the isolation film 51 for isolating the adjacent ultrasonic transducers 10 (space parts 6 or recesses 22) from each other.

By forming the groove 23 in the land part 21, the adjacent ultrasonic transducers 10 (space parts 6 or recesses 22) communicate with each other. The process of vapor-depositing the vapor-deposition object is performed in a vacuum as mentioned later, and air does not usually approximately exist in the space part 6, but there is a possibility that a trace amount of air may exist depending on the degree of vacuum. In a case where such a trace amount of air moves between the adjacent ultrasonic transducers 10 (space parts 6 or recesses 22) via the groove 23 when the ultrasonic transducer 10 is operated, the vibration in each ultrasonic transducer 10 has an acoustic and mechanical impact on the vibration in the other ultrasonic transducers 10, thereby causing electrical noise.

However, the above problems can be prevented in advance by the isolation film 51 formed via the through hole 11 near the groove 23 by the process of the vapor deposition, in the ultrasonic transducer unit and the ultrasonic probe according to Embodiment 1 of the present invention.

In detail, as shown in FIG. 8, the isolation film 51 is formed near the groove 23 by vapor-depositing the vapor-deposition object. The isolation film 51 has a form of a rectangular recess in the cross section in the same manner as the through hole 11. Note that the isolation film 51 seals the vacuum state of the structure from the end part 24 of one land part 21 to the end part 24 of the other land part 21. Therefore, the isolation film 51 completely isolates a space between the adjacent ultrasonic transducers 10 (space parts 6 or recesses 22). When the ultrasonic transducer 10 is operated, even a trace amount of air is prevented from moving between the adjacent ultrasonic transducers 10 (space parts 6 or recesses 22) via the groove 23, and the mechanical vibration to the adjacent ultrasonic transducer 10 and the transfer of an acoustic wave can be prevented.

On the other hand, when the actions of the CMT (Capacitive Micromachined Transducer) or the CMUT are interpreted from a viewpoint of energy, the actions are actions for converting the electric energy (driving current) to the mechanical energy (sound pressure or vibration of the vibrating membrane), and the conversion is also reversibly performed. An electro-mechanical coupling coefficient is used as a function showing the efficiency in such a conversion. The conversion efficiency or the electro-mechanical coupling coefficient can be expressed with the proportion of a fixed capacitance to a capacitance variation, and it can be said that the larger the conversion capacitance is as compared with the fixed capacitance, the larger the conversion efficiency is.

When this is applied to the ultrasonic transducer of the ultrasonic transducer unit according to Embodiment 1 of the present invention, the fixed capacitance can be expressed as the sum of the basic capacitance occurring at the vibrating membrane and the substrate-side electrode and the parasitic capacitance occurring based on a cross point of the electrode etc. and independent of the vibration of the vibrating membrane. The conversion capacitance means to be the capacitance occurring only by the vibration of the vibrating membrane. Therefore, as the parasitic capacitance is larger, the conversion efficiency or the electro-mechanical coupling coefficient decreases.

On the other hand, in the ultrasonic transducer unit and the ultrasonic probe according to Embodiment 1 of the present invention, since the isolation film 51 is vapor-deposited to a connection portion (connection electrode 31) in which the substrate-side electrodes 3 of the adjacent ultrasonic transducers 10 are connected to each other via the through hole 11, the parasitic capacitance occurring at the connection portion of the substrate-side electrodes 3 can be prevented at the maximum, and the sensitivity can be improved at the maximum. That is, the influence by the parasitic capacitance occurring between the vibrating membrane 1 and the connection electrode 31 can be prevented near the groove 23.

Although the above description has explained the case in which the vibrating membrane 1 made of the electric-conductivity material is provided, in other words, the vibrating membrane 1 functions as a film-side electrode as an example, it is not restricted to this and a film-side electrode may be further provided on the vibrating membrane 1.

In this case, needless to say, the effect that the occurrence of the parasitic capacitance between the vibrating membrane 1 and the connection electrode 31 near the groove 23 is controlled by the isolation film 51 is brought about.

In the ultrasonic probe according to Embodiment 1 of the present invention, voltage is applied between the substrate-side electrodes 3 and the vibrating membranes 1 of the plurality of ultrasonic transducers 10 provided in the ultrasonic transducer unit to transmit an ultrasonic wave to the outside. An electric signal concerning the change of the electrostatic capacitance between the substrate-side electrodes 3 and the vibrating membranes 1 involved in the vibration of the substrate 2 (or the vibrating membrane 1) due to the ultrasonic wave reflected from the outside can be obtained, and a so-called ultrasonic image can be obtained based on the electric signal.

The following description explains a method of manufacturing the ultrasonic transducer unit (ultrasonic transducer) according to Embodiment 1 of the present invention.

For example, an upper face of a substrate 2 made of the Pyrex glass is patterned to form a recess 22. Both of a land part 21 and a groove 23 are formed when the substrate 2 is patterned. In this case, a hollow for burying a substrate-side electrode 3 is also formed in a central portion of the bottom of the recess 22, and both hollows for burying a connection electrode 31 are also formed in the bottom of the recess 22 and the bottom of the groove 23.

Subsequently, the vapor-deposition object (for example, Ni, Cr, Al, Pt, Au, etc.) for the substrate-side electrode 3 and the connection electrode 31 is vapor-deposited. Moreover, an insulating film 4 and an insulating film 41 for insulating the substrate-side electrode 3 and the connection electrode 31 from the vibrating membrane 1 are formed by the vapor deposition, respectively.

Then, a SOI (Silicon On Insulator) wafer is fixed to the upper face of the substrate 2, i.e., the upper face of the land part 21, so that one face of the SOI wafer faces the upper face of the substrate 2 (or the bottom of the recess 22). The fixing is performed by the anodic bonding method.

Then, the wet etching is performed with respect to the other face of the SOI wafer, i.e. an oxide layer, and a Si layer using TMAH, KOH, HF, etc., to remove excluding a portion for the vibrating membrane 1 so as to form the vibrating membrane 1. Thereby, the vibrating membrane 1 is fixed to the land part 21 by the electrostatic attraction and the chemical bond.

Thus, the vibrating membrane 1 made of silicon single crystal is fixed to the upper face of the glass land part 21 (the substrate 2) by the anodic bonding method at a lower temperature compared with the other bonding method. Therefore, the occurrence of the stress due to the deformation created by the bonding at a high temperature can be prevented and also the occurrence of the stress by a so-called dissimilar thin film bonding can be controlled since the thermal expansion coefficients of the vibrating membrane 1 and the land part 21 are almost same.

Subsequently, the etching is performed using an etching mask to form a through hole 11 in the vibrating membrane 1. Then, an insulating vapor-deposition object is vapor-deposited in a vacuum to form a protective film 5. In this case, an isolation films 51 is also formed since the vapor-deposition object is vapor-deposited via the through hole 11 on the inner side and the vicinity of the groove 23 as mentioned above.

Note that it is not restricted to this, and a Si wafer having a Si/$Si_3N_4$ (low stress) configuration may be used instead of the SOI wafer.

Therefore, the ultrasonic transducer unit and the ultrasonic probe according to Embodiment 1 of the present invention do not require the process of forming a sacrificial layer, the process of forming a hole, the process of etching the sacrificial layer, the process of burying the hole, etc., as compared with the conventional manufacturing process. Thereby the number of processes decreases and also the time required can also be shortened, and the effect of reducing the manufacturing cost is brought about.

Since it is not necessary to provide separately the so-called vibrating membrane supporting section which supports the vibrating membrane 1 so as to vibrate, the number of processes further decreases. Moreover, it is not necessary to consider the stress concentration in a fixed portion occurring when the vibrating membrane supporting section is fixed to the substrate, and the manufacturing flexibility is broadened.

The following description explains an action of the ultrasonic unit (ultrasonic transducer 10) according to Embodiment 1 of the present invention. For convenience of explanation, the description explains a case in which voltage is applied to the ultrasonic transducer 10 to transmit an ultrasonic wave towards an object, and the ultrasonic wave reflected from the object is received.

When the ultrasonic transducer 10 of the ultrasonic transducer unit according to Embodiment 1 of the present invention receives an ultrasonic wave reflected from the object, the vibrating membrane 1 vibrates by the ultrasonic wave (sound pressure). When the vibrating membrane 1 vibrates, a space between the vibrating membrane 1 and the substrate-side electrode 3 of the substrate 2 changes. Therefore, the electrostatic capacitance between the vibrating membrane 1 and the substrate-side electrode 3 also changes. The change of the electrostatic capacitance between the vibrating membrane 1 and the substrate-side electrode 3 can be converted to a voltage change signal to obtain an electric signal, and an ultrasonic image of the object can be obtained based on the obtained electric signal.

When an ultrasonic wave is transmitted, DC voltage and AC voltage are applied between the vibrating membrane 1 and the substrate-side electrode 3, and thereby the vibrating membrane 1 vibrates to transmit an ultrasonic wave. The other actions are the same as those of the case in which an ultrasonic wave is received, and detailed description thereof is omitted.

Embodiment 2

Figure 9:
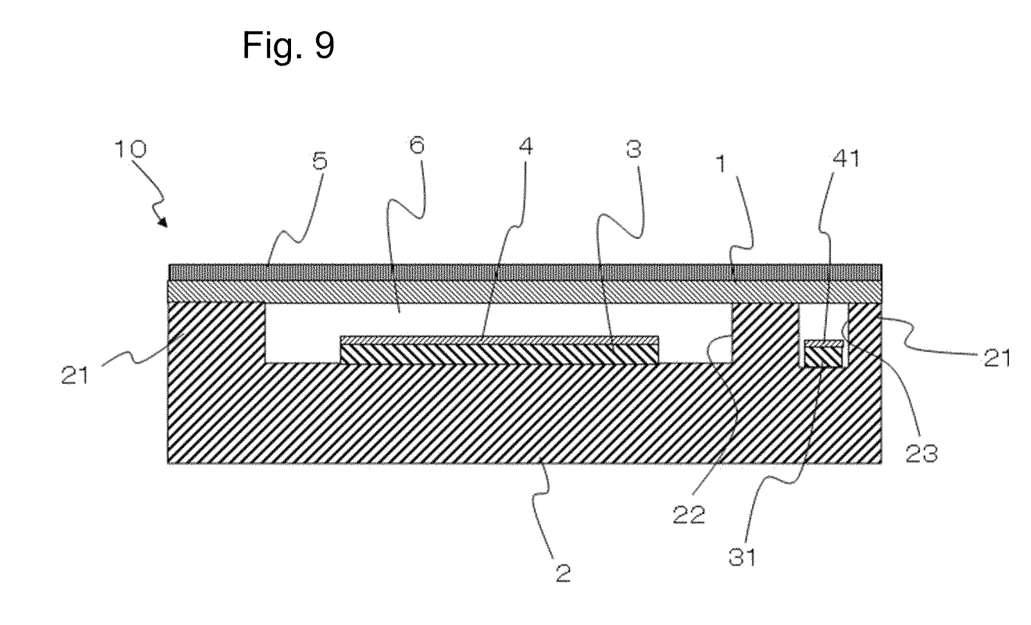
FIG. 9 is a schematic sectional view for explaining a configuration of an ultrasonic transducer provided in an ultrasonic transducer unit according to Embodiment 2 of the present invention.

FIG. 9 is a schematic sectional view for explaining a configuration of an ultrasonic transducer provided in an ultrasonic transducer unit according to Embodiment 2 of the present invention. The ultrasonic transducer 10 of the ultrasonic transducer unit according to Embodiment 2 of the present invention comprises a substrate 2, and a vibrating membrane 1 which is arranged on an upper side of the substrate 2 to face the substrate 2 and transmits or receives an ultrasonic wave. A protective film 5 for protecting the vibrating membrane 1 is vapor-deposited on an upper face of the vibrating membrane 1, and a recess 22 is formed on an upper face of the substrate 2 facing a lower face of the vibrating membrane 1. A substrate-side electrode 3 protrudes on a bottom of the recess 22.

A plurality of the ultrasonic transducers 10 of such a configuration are provided on the upper face of the substrate 2 in a pattern state, and function as the ultrasonic transducer unit according to Embodiment 2 of the present invention.

The tubular recess 22 having a hexagonal form in a plane view is formed on the upper face of the substrate 2, and the protruding substrate-side electrode 3 is formed in a central portion of the bottom of the recess 22 by vapor deposition. A land part 21 consisting of a residual part of the substrate 2 which is remaining after forming the recesses 22 is formed between the adjacent recesses 22. A plurality of grooves 23 are formed at a plurality of sites of the land part 21 by cutting parts of the land part 21 in a lengthwise direction. A protruding connection electrode 31 connecting the adjacent substrate-side electrodes 3 to each other is also formed on the bottom of the groove 23 by vapor deposition. That is, the connection electrode 31 protrudes over the bottoms of the recess 22 and the groove 23.

An insulating film 4 which is made of an oxide, for example, and insulates the substrate-side electrode 3 from the vibrating membrane 1 is vapor-deposited on an upper face of the substrate-side electrode 3. An insulating film 41 which insulates the connection electrode 31 from the vibrating membrane 1 is vapor-deposited on an upper face of the connection electrode 31, in the same manner as the substrate-side electrode 3. The connection electrodes 31 extend from edges of the substrate-side electrodes 3 having a hexagonal form in a plane view in a plane direction of the substrate-side electrodes 3, respectively.

A lower face of the vibrating membrane 1 is bonded on an upper face of the land part 21 by the anodic bonding method.

The other configuration is the same as that of Embodiment 1, and detailed description thereof is omitted.

The same parts as in Embodiment 1 are designated with the same reference numbers, and detailed explanation thereof will be omitted.

Figure 10:
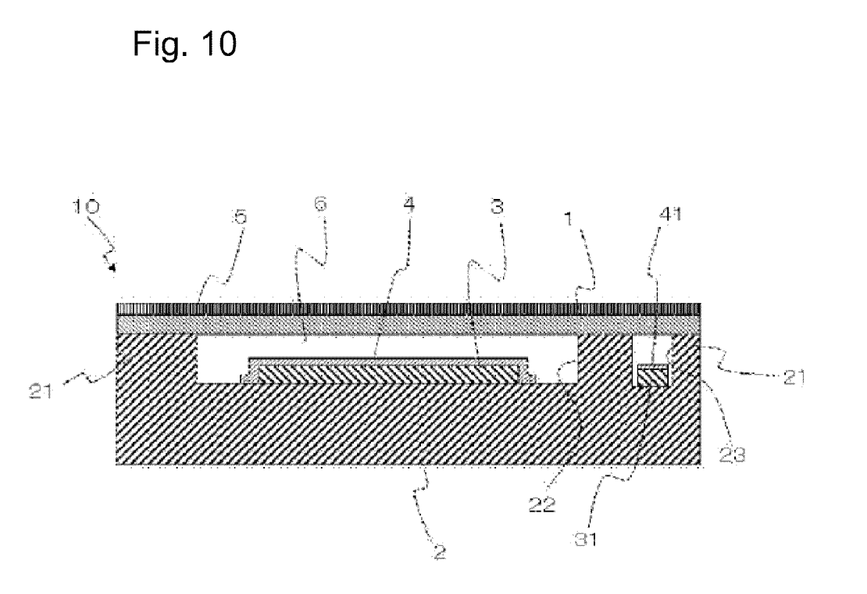
FIG. 10 a schematic sectional view for explaining a configuration of an ultrasonic transducer provided in an ultrasonic transducer unit according to Embodiment 3 of the present invention.

FIG. 10 a schematic sectional view for explaining a configuration of an ultrasonic transducer provided in an ultrasonic transducer unit according to Embodiment 3 of the present invention. The ultrasonic transducer 10 of the ultrasonic transducer unit according to Embodiment 3 of the present invention comprises a substrate 2, and a vibrating membrane 1 which is arranged on an upper side of the substrate 2 to face the substrate 2 and transmits or receives an ultrasonic wave, and is configured in the same manner as Embodiment 2.

On the other hand, in Embodiment 3, an insulating film 4 which is made of an oxide, for example, and insulates the substrate-side electrode 3 from the vibrating membrane 1 is vapor-deposited so as to cover the substrate-side electrode 3. In detail, the insulating film 4 covers an upper face and a side face of the substrate-side electrode 3 and a part of a bottom of the recess 22. The other configuration is the same as that of Embodiment 1, and detailed description thereof is omitted.

The same parts as in Embodiment 1 are designated with the same reference numbers, and detailed explanation thereof will be omitted.

EXPLANATION OF REFERENCES

1 Vibrating membrane
2 Substrate
3 Substrate-side electrode
4 Insulating film
5 Protective film
6 Space part
10 Ultrasonic transducer
11 Through hole
21 Land part
22 Recess
23 Groove
31 Connection electrode
41 Insulating film
51 Isolation Film

What is claimed is:

1. An ultrasonic transducer unit comprising a plurality of ultrasonic transducers on an insulating substrate, each of the ultrasonic transducers which is provided with a substrate-side electrode provided on one face side of the substrate and with a vibrating membrane having an electric conductivity and arranged so that one face of the vibrating membrane faces the substrate-side electrode, wherein
said ultrasonic transducer is provided with:
a land part which protrudes from the one face side of the substrate and is made of the same material as that of the substrate; and
a recess formed from the substrate and the land part,
said substrate-side electrode is provided in a bottom of the recess, and
said vibrating membrane is provided so as to cover the recess.

2. The ultrasonic transducer unit according to claim 1, wherein said vibrating membrane is fixed to a land part by electrostatic attraction and chemical bonding.

3. The ultrasonic transducer unit according to claim 2, wherein said substrate-side electrode is buried in the bottom of the recess,
a groove which connects the recesses of the ultrasonic transducers is formed in the land part, and a connection electrode which connects the substrate-side electrodes of the ultrasonic transducers is buried in a bottom of the groove and the bottom of the recess.

4. The ultrasonic transducer unit according to claim 2, wherein said substrate-side electrode protrudes in the bottom of the recess,
   a groove which connects the recesses of the ultrasonic transducers is formed in the land part, and
   a connection electrode which connects the substrate-side electrodes of the ultrasonic transducers to each other protrudes in a bottom of the groove and the bottom of the recess.

5. The ultrasonic transducer unit according to claim 3, wherein a through hole is formed in the vibrating membrane at a position conforming the groove,
   a protective film including an object which is vapor-deposited is formed on the other side of the vibrating membrane, and
   an isolation film including an object which is vapor-deposited via the through hole, and isolating the adjacent ultrasonic transducers from each other is formed inside the groove.

6. The ultrasonic transducer unit according to claim 1, wherein said vibrating membrane is fixed to the land part by an anodic bonding method.

7. The ultrasonic transducer unit according to claim 1, wherein the vibrating membrane includes silicon single crystal.

8. An ultrasonic probe comprising an ultrasonic transducer unit according to claim 1, wherein the ultrasonic probe sends and receives an ultrasonic wave using said ultrasonic transducer unit.

* * * * *